(12) United States Patent
Tatsumi (10) Patent No.: US 12,102,351 B2
(45) Date of Patent: Oct. 1, 2024

(54) SURGICAL PROBE INCORPORATING A DILATOR

(71) Applicant: GLOBUS MEDICAL, INC., Audubon, PA (US)

(72) Inventor: Robert Louis Tatsumi, Lake Oswego, OR (US)

(73) Assignee: Globus Medical, Inc., Audubon, PA (US)

( * ) Notice: Subject to any disclaimer, the term of this patent is extended or adjusted under 35 U.S.C. 154(b) by 86 days.

(21) Appl. No.: 17/933,916

(22) Filed: Sep. 21, 2022

(65) Prior Publication Data

US 2023/0012760 A1    Jan. 19, 2023

Related U.S. Application Data (63) Continuation of application No. 16/942,840, filed on Jul. 30, 2020, now Pat. No. 11,478,271, which is a continuation of application No. 15/728,659, filed on Oct. 10, 2017, now Pat. No. 10,758,266, which is a continuation of application No. 13/841,981, filed on Mar. 15, 2013, now Pat. No. 9,814,488.

(51) Int. Cl.
| | |
|---|---|
| A61B 17/34 | (2006.01) |
| A61B 5/00 | (2006.01) |
| A61B 17/00 | (2006.01) |
| A61B 17/16 | (2006.01) |
| A61B 17/32 | (2006.01) |
| A61N 1/05 | (2006.01) |

(52) U.S. Cl.
CPC ...... *A61B 17/3421* (2013.01); *A61B 17/3439* (2013.01); *A61B 5/4893* (2013.01); *A61B 2017/00261* (2013.01); *A61B 17/1626* (2013.01); *A61B 2017/320048* (2013.01); *A61N 1/0551* (2013.01)

(58) Field of Classification Search
CPC ............ A61B 17/3439; A61B 17/3421; A61B 17/885; A61B 17/8852; A61B 17/8855; A61B 17/8858
See application file for complete search history.

(56) References Cited

U.S. PATENT DOCUMENTS

| | | |
|---|---|---|
| 5,409,483 A | 4/1995 | Campbell et al. |
| 6,564,078 B1 | 5/2003 | Marino et al. |
| 6,607,547 B1 | 8/2003 | Chin |
| 7,079,883 B2 | 7/2006 | Marino et al. |
| 8,489,170 B2 | 7/2013 | Marino et al. |
| 9,014,776 B2 | 4/2015 | Marino et al. |
| 2003/0158464 A1 | 8/2003 | Bertolero |
| 2006/0184223 A1 | 8/2006 | Squicciarini |
| 2010/0010334 A1 | 1/2010 | Bleich et al. |

FOREIGN PATENT DOCUMENTS

| | | |
|---|---|---|
| JP | 2003524452 A | 8/2003 |
| JP | 2013523413 A | 6/2013 |
| WO | 2013067179 A2 | 5/2013 |

*Primary Examiner* — Olivia C Chang (57) ABSTRACT

A surgical probe and a method for forming and enlarging an access opening through a psoas muscle to provide for minimally invasive lateral approach for surgical access to a lumber intervertebral disc. A distal end portion of the probe is equipped with an electrode useful for confirming proper location of the probe and includes an inflatable dilator body for enlarging an access opening through tissue adjacent to a spinal column. The probe includes a cannula through which a K wire can be extended to anchor the probe to a patient.

10 Claims, 9 Drawing Sheets

SURGICAL PROBE INCORPORATING A DILATOR

CROSS-REFERENCE TO RELATED APPLICATIONS

This application is a divisional application of U.S. patent application Ser. No. 16/942,840 filed on Jul. 30, 2020, which is a continuation of U.S. patent application Ser. No. 15/728,659, filed on Oct. 10, 2017, which is a continuation of U.S. patent application Ser. No. 13/841,981 filed on Mar. 15, 2013, (published as U.S. Patent Publication No. 2014-0276869), which is incorporated herein by reference in its entirety for all purposes.

BACKGROUND

The present invention relates to surgical procedures, and in particular to a probe incorporating a dilator and a method for its use in connection with minimally invasive surgery.

Minimally invasive surgery techniques have been used in the past for spinal disc replacement procedures.

There are known devices for dilatation of soft tissue structures of the human body, including blood vessels, other ducts, bowels, and other lumens. Certain dilators are known to incorporate inflatable members utilized to separate soft tissue, including muscular tissue, in order to provide visibility and access to portions of the anatomy that are of interest.

In some surgical procedures it is important to determine where certain structures are located in order not to damage them. For example, it is desired not to sever nerves or some blood vessels or other ducts or conduits for fluid. While fluoroscopy can be used to guide surgeons in the placement of probes used to guide certain types of dilators, other techniques are often desirable for determining exactly where a surgical instrument should be placed in order to avoid damaging structures such as nerves.

In preparing for spinal disc replacement or spinal fusion using minimally invasive surgical procedures, a probe may be equipped with an electrode on its tip, with a suitable electrical conductor being connected to the electrode and extending along the probe to a proximal part. An electrical signal can be supplied through the electrode and a resulting response can be interpreted to identify nerves, vascular, and muscular structures in the vicinity of the electrode on the distal tip of the probe.

Presently utilized procedures in connection with a lateral approach to a lumbar spinal disc require creation of a pathway through the psoas major muscle to obtain access to a diseased intervertebral disc. Dilatation of an opening made through the psoas muscle is required to provide access to a patient's spinal column and has been performed in the past by placing successively larger tubular dilators over and along a probe, until a suitably large dilator has been moved into place. This, however, requires an appreciable amount of time and results in undesirable amount of trauma to the tissue between the incision where the probe has been inserted and the required dilated opening through the psoas muscle and other tissues surrounding the spinal column.

What is desired, then, is an improved way to form and dilate an opening through soft tissue, precisely in a required location, in order to provide necessary workspace in which to perform a surgical procedure, yet avoid damage to critical tissue such as nerves surrounding an opening through which a minimally invasive surgical procedure is to be performed.

SUMMARY OF THE DISCLOSURE

In accordance with the present invention, defined by the claims which form a part of this application, a device is provided by means of which access can be provided through intervening soft tissue to an anatomical structure of interest, and a method for use of the device is also disclosed.

In one embodiment of the device disclosed herein, a cannulated probe incorporates an electrode by which an electrical signal can be supplied during insertion of the probe, to assist in proper placement and thereby avoid damage to critical structures in the vicinity of the probe.

In one embodiment of the device disclosed herein, such a cannulated probe incorporates a dilator in which an inflatable member surrounds a cannula portion of the probe and expands radially outwardly, to displace surrounding soft tissue when the probe is in a selected location and thereby provide space adjacent to an anatomical structure where surgical attention is required, permitting visualization of structures upon which a surgical procedure might be performed.

In accordance with one embodiment of the method disclosed herein, a cannulated probe is inserted from a surgical opening through a patient's skin toward an intervertebral disc that is to be surgically treated. The probe is directed and pushed through a portion of a psoas muscle and an electrode incorporated in a tip of the probe is used to confirm correct location of the probe. Thereafter, a tip portion of the probe is inflated to dilate an opening through tissue adjacent to the patient's spine, including the psoas muscle.

The foregoing and other objectives, features, and advantages of the invention will be more readily understood upon consideration of the following detailed description of the invention, taken in conjunction with the accompanying drawings.

DETAILED DESCRIPTION OF EMBODIMENTS

Referring to FIGS. 1-6 of the drawings, a probe 20 which is a first exemplary embodiment of the device disclosed herein includes a main body having a proximal end portion 22 and a distal end portion 24 that may be tapered to a relatively sharp end. The probe 20 is shown with its transverse, or lateral, dimensions considerably exaggerated, for the sake of clarity. In one embodiment the main body may be of a molded polymeric plastic resin material. Exposed at the extreme distal tip and extending a short distance along the distal end portion 24 there is an electrode 26. A centrally located cannula 28 extends longitudinally through the probe 20, with a central bore extending from the proximal end 22 to and through the distal end portion 24, as may be seen best in FIG. 3.

Figure 1:
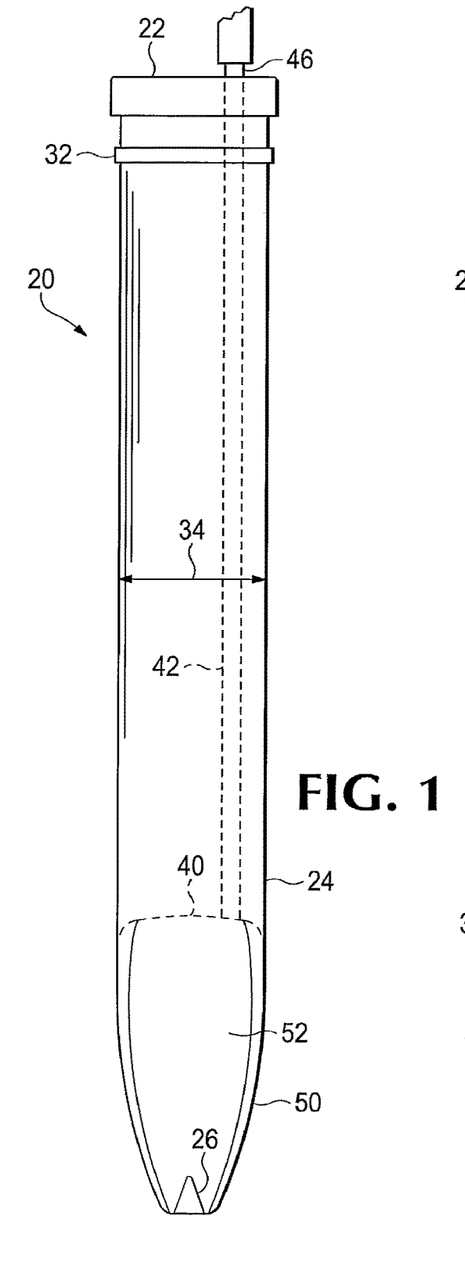
FIG. 1 is a side elevational view of a combined probe and dilator which is an embodiment of an aspect of the present invention.
Figure 2:
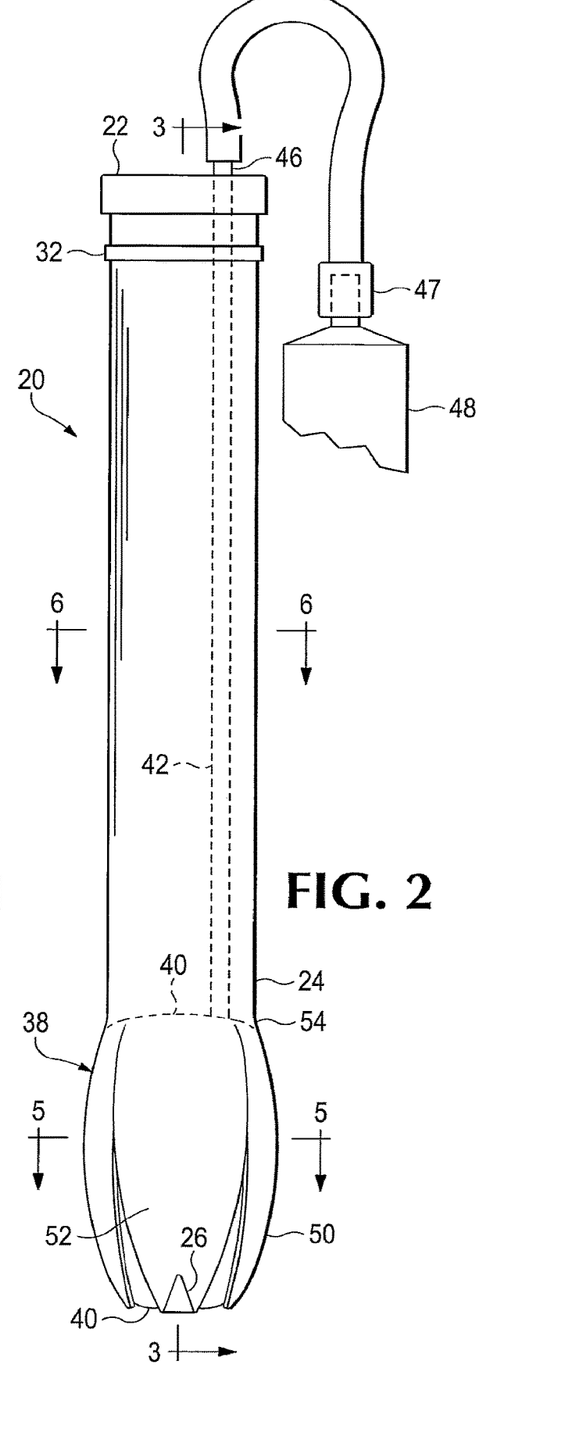
FIG. 2 is a side elevational view of the probe and dilator shown in FIG. 1, also showing a syringe used to inflate and expand a distal tip portion of the probe.

An insulated electrical conductor 30 is connected electrically with the electrode 26, extending within the body of the probe 20, and is electrically connected with a terminal 32 such as a ring of electrically conductive material located externally at the proximal end 22 of the main body and available to receive an electrical signal, as from a stimulator (not shown), as will be explained presently. The main body of the probe 20 may have a diameter 34 of, for example, 6 to 8 millimeters.

The distal end portion 24 of the probe 20 acts as a dilator 38, as follows. A bladder 40 may be located in the distal end portion 24, surrounding the cannula 28. A fluid conduit 42 is connected to the bladder 40, communicating with an interior space 44 within the bladder 40, and extends toward the proximal end portion 22 of the main body. A port 46, to which the conduit 42 is connected, may include a suitable connector, such as a Luer connector 47, to receive and conduct fluid to the interior 44 of the bladder 40, as from a syringe 48 shown in FIG. 2. If desired, such a Luer connector 47 can be used to facilitate separation of the source of fluid from the probe 20 while retaining the fluid within the conduit 42 and the bladder 40. A suitable, preferably noncompressible, fluid such as sterile saline or compressed air may be utilized to inflate and expand the bladder 40. The bladder 40 may be made of flexible and elastic material such as Silastic, or other biocompatible rubber-like synthetic plastic material.

Figure 3:
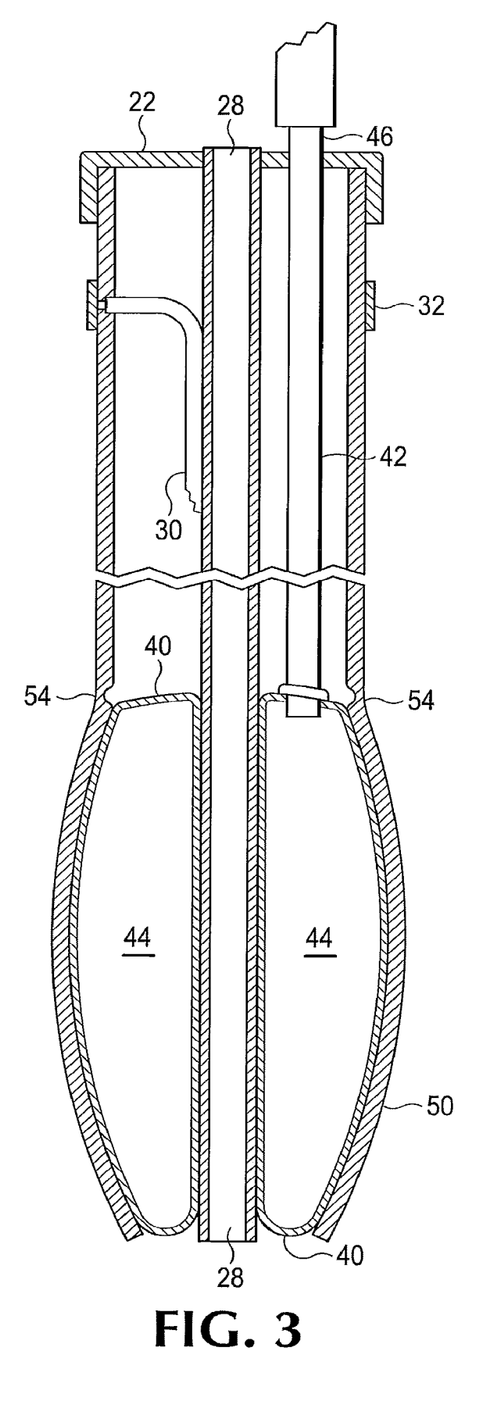
FIG. 3 is a sectional view taken along line 3-3 of FIG. 2.
Figure 4:
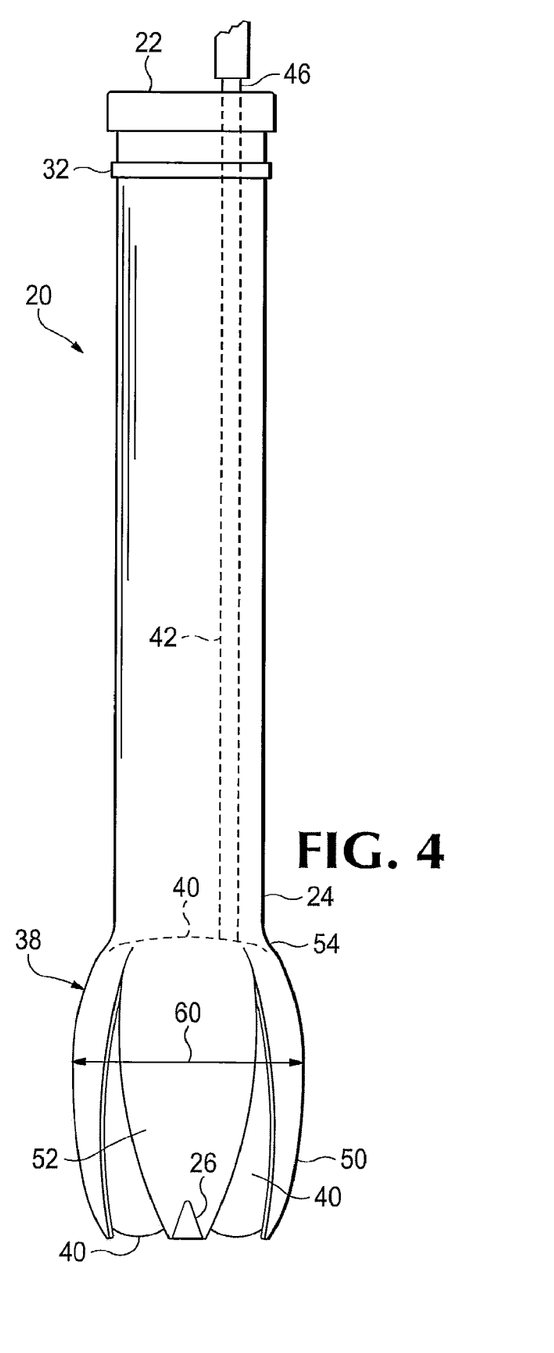
FIG. 4 is a side elevational view of the probe and dilator shown in FIG. 1, with its distal tip portion expanded to a greater degree than shown in FIG. 2.
Figure 5:
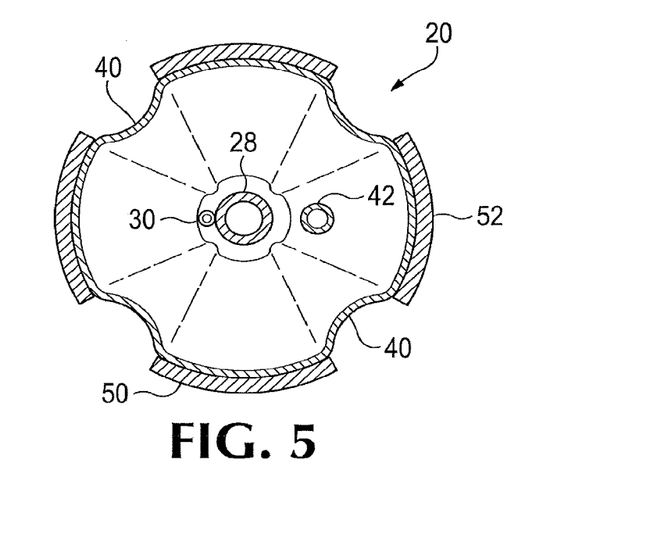
FIG. 5 is a sectional view taken along line 5-5 in FIG. 4.
Figure 6:
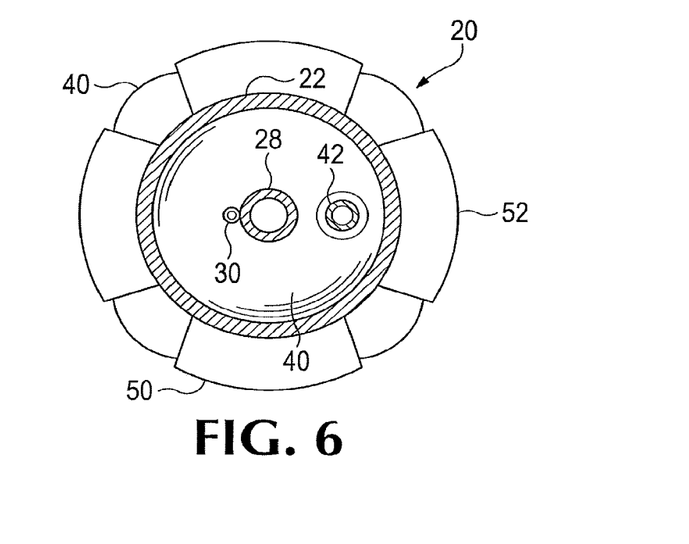
FIG. 6 is a sectional view taken along line 6-6 in FIG. 4.
Figure 7:
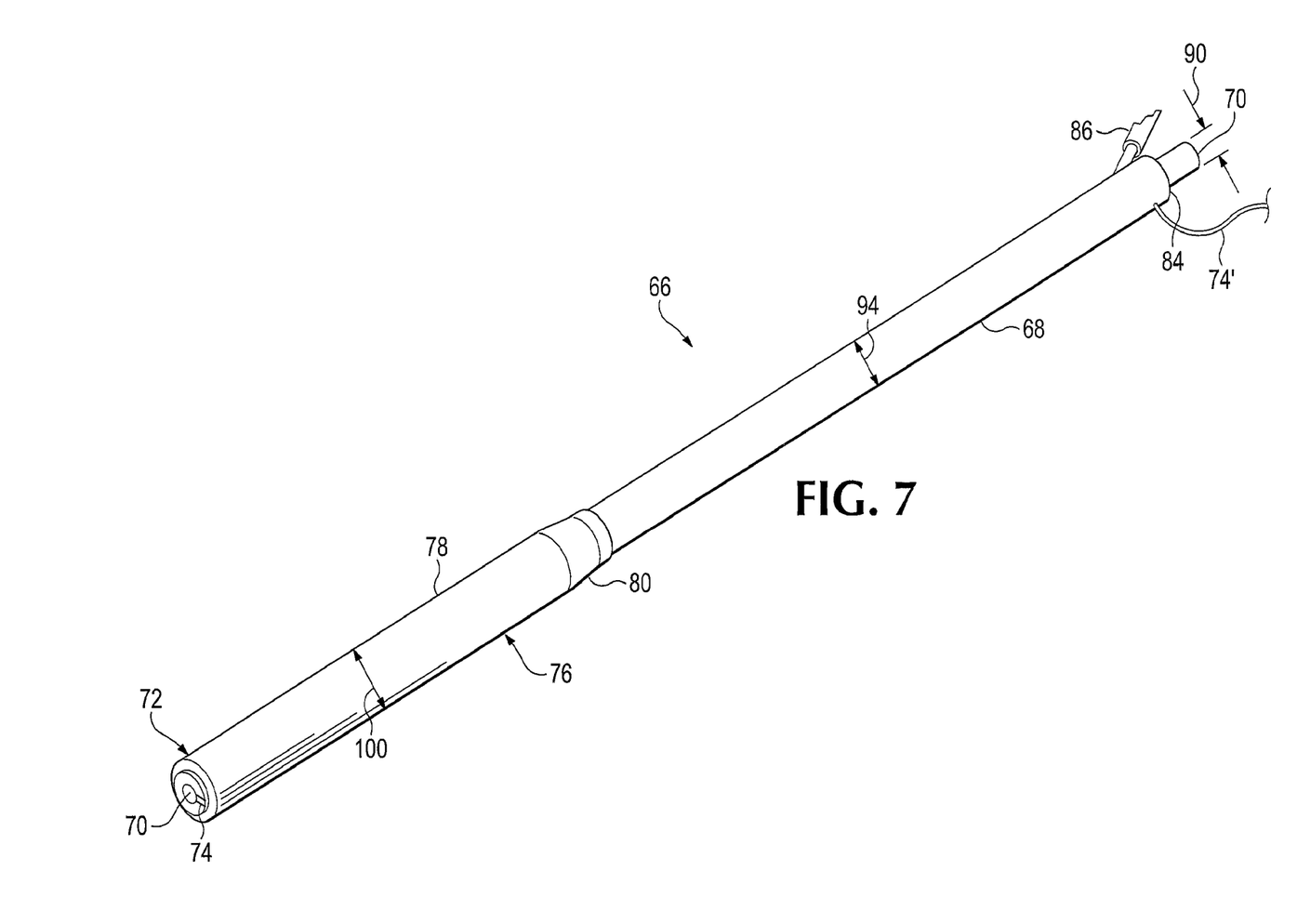
FIG. 7 is an isometric view taken from the distal end of a probe and dilator which is an alternative embodiment of the device disclosed herein.

The distal end portion 24 of the main body may be divided along longitudinal radial planes to define several sectors 50, 52, etc., each connected to the main body portion of the probe 20, as by a flexible connector such as hinges 54 as shown in section view in FIG. 3. The hinges 54 may, for example, be "live" hinges formed as reduced thickness portions of a wall of the main body made of a somewhat elastic and flexible plastic resin material. The hinges 54 permit the distal tips of the sectors 50, 52, etc. to move radially and outwardly apart from the cannula in response to inflation of the bladder 40, to a position such as those shown in FIGS. 2, 4 and 5. For example, the bladder 40 may be inflated to expand the distal end portion 24 from its original diameter 34 by several millimeters, to a diameter as large as, for example, 12 to 14 millimeters, as shown in FIG. 4 at 60.

Referring next to FIGS. 7-11, a somewhat different probe 66 has a main body portion 68, and a cannula 70 of an electrically insulative material such as a suitable plastic resin extends from the proximal end for the full length of the probe 66 and within a distal end portion 72. An electrode 74 is located and exposed at the distal end 72 of the probe 66. The cannula 70 may be constructed as a thin-walled tube of a suitable plastic resin. An insulated electrical conductor 75 extends along the exterior surface of the cannula 70 from the electrode 74 to a terminal 74' near the proximal end of the probe 66 in the annular space between the main body portion 68 and the cannula 70. An elastically expansible dilator 76 in the form of a balloon or bladder 78 that may be generally cylindrical in shape surrounds the cannula 70 at the distal end of the probe 66 and is sealingly attached to the cannula 70 at the distal end portion 72. A proximal end 80 of the bladder 78 may be tapered as shown best in FIGS. 8 and 9 and is sealingly and securely attached to an exterior surface of a tubular outer portion 82 of the main body portion 68 that surrounds the cannula 70. A proximal end 84 of the tubular portion 82 is connected to the cannula 70 in a sealing, fluid-tight, manner, although there is sufficient radial space between the cannula 70 and the interior of the tubular outer portion 82 to conduct fluid such as a saline solution or air from a port or connector 86 to the interior of the bladder 76.

Figure 8:
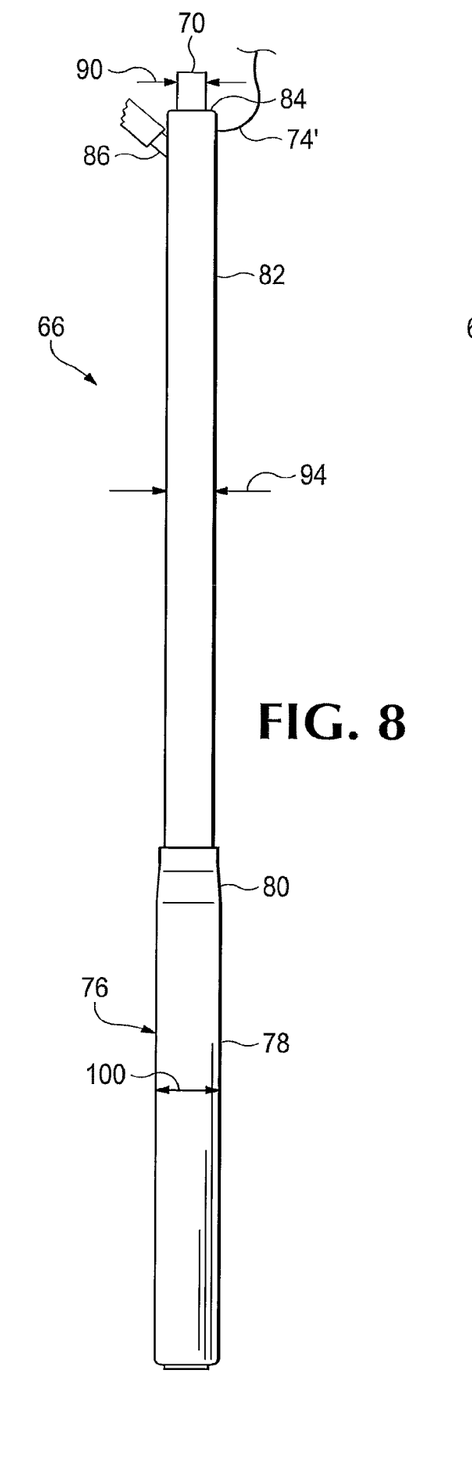
FIG. 8 is a perspective side view of the probe and dilator shown in FIG. 7.
Figure 9:
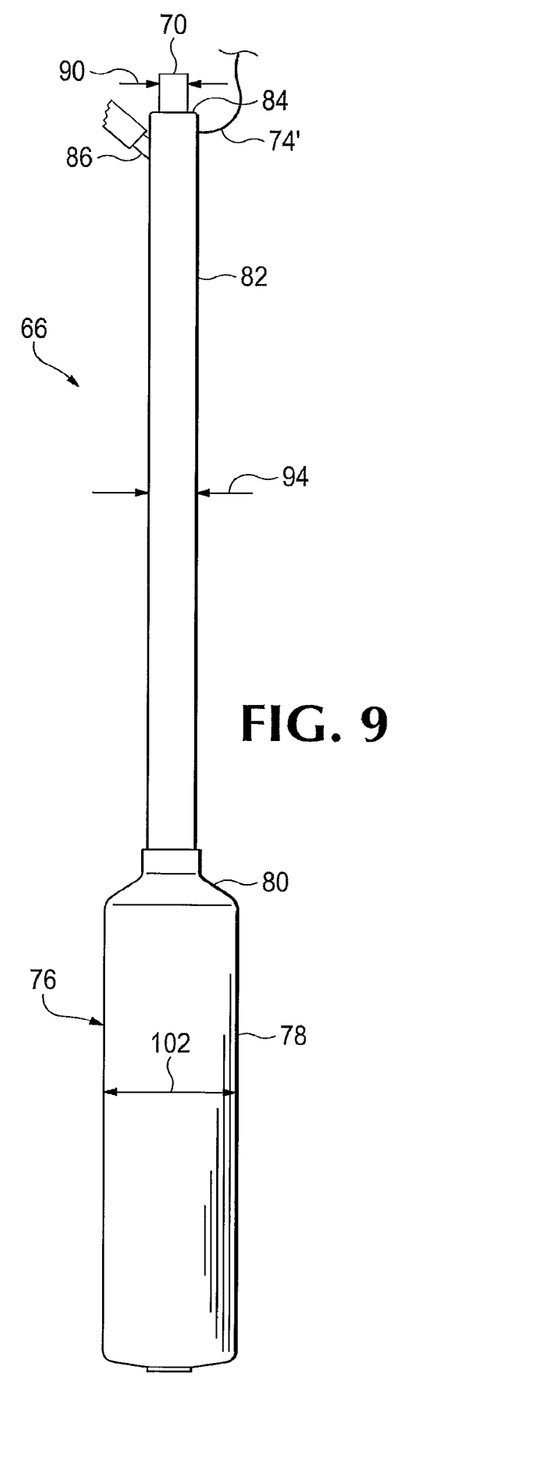
FIG. 9 is a view similar to FIG. 8, showing a distal end portion of the probe and dilator expanded in an inflated/expanded condition.
Figures 10, 11:
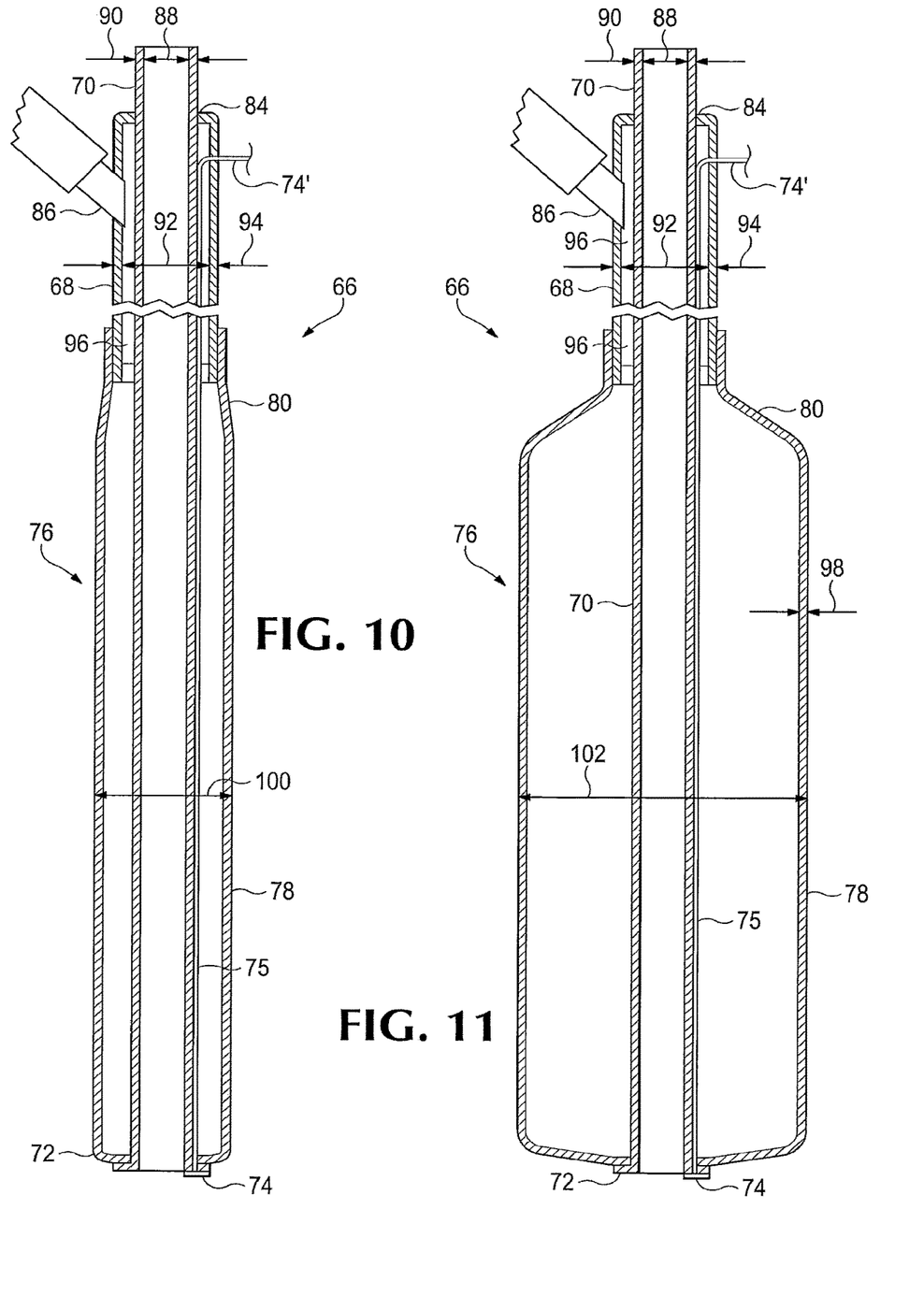
FIG. 10 is a sectional view showing the interior structure of the probe and dilator shown in FIG. 7, in the configuration shown in FIG. 8.
FIG. 11 is a sectional view of the probe and dilator shown in FIG. 7 with the distal end portion expanded as shown in FIG. 9.

For example, the cannula 70 may have an internal diameter 88 of 2.0 millimeters and an outer diameter 90 of 3.0 millimeters, while the tubular outer body portion 82 of the main body portion 68 may have an internal diameter 92 of 3.40 millimeters and an outer diameter 94 of 4.40 millimeters, leaving an annular space 96 with a radial dimension of 0.2 millimeters through which the electrical conductor 75 extends and through which fluid can be conducted from the connector 86 to the interior of the bladder 78. In one embodiment, the bladder 78 may be formed of an elastomeric membrane of an elastic plastic resin, for example, a PET or Bayer Texin 985™, and may have a wall thickness 98 of 0.5 millimeters and a diameter 100 of 6.0 millimeters when in a relaxed, not expanded, condition, as shown in FIGS. 8 and 9, and a diameter 102 of 12.0 millimeters, when inflated as shown in FIGS. 9 and 11. A suitably shaped mesh or fabric of a relatively inelastic material may be embedded in the material of the wall of the bladder 78 to limit its expansion and define its shape to be generally cylindrical when in an expanded condition as shown in FIGS. 9 and 11.

Figure 12:
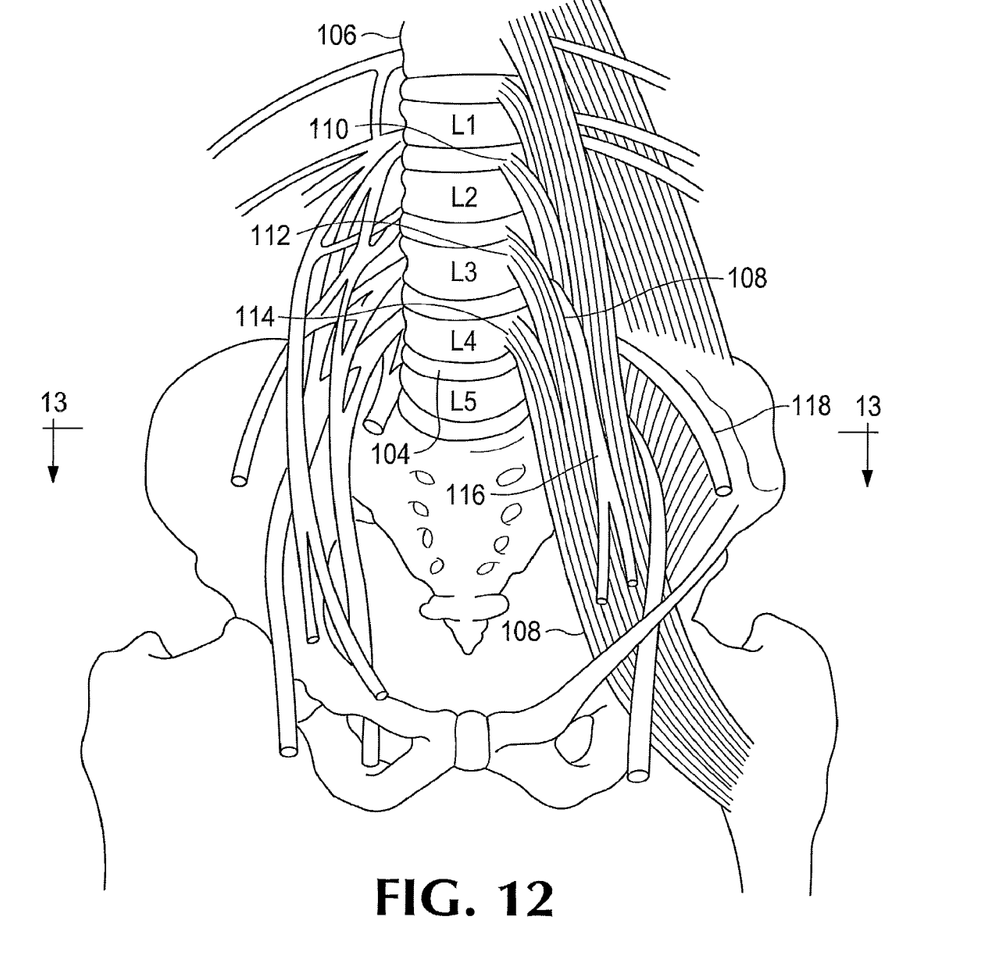
FIG. 12 is a simplified view of a portion of a human skeleton including lumbar spine, pelvic girdle, and upper femurs, and showing some associated musculature and nerve structures.
Figure 13:
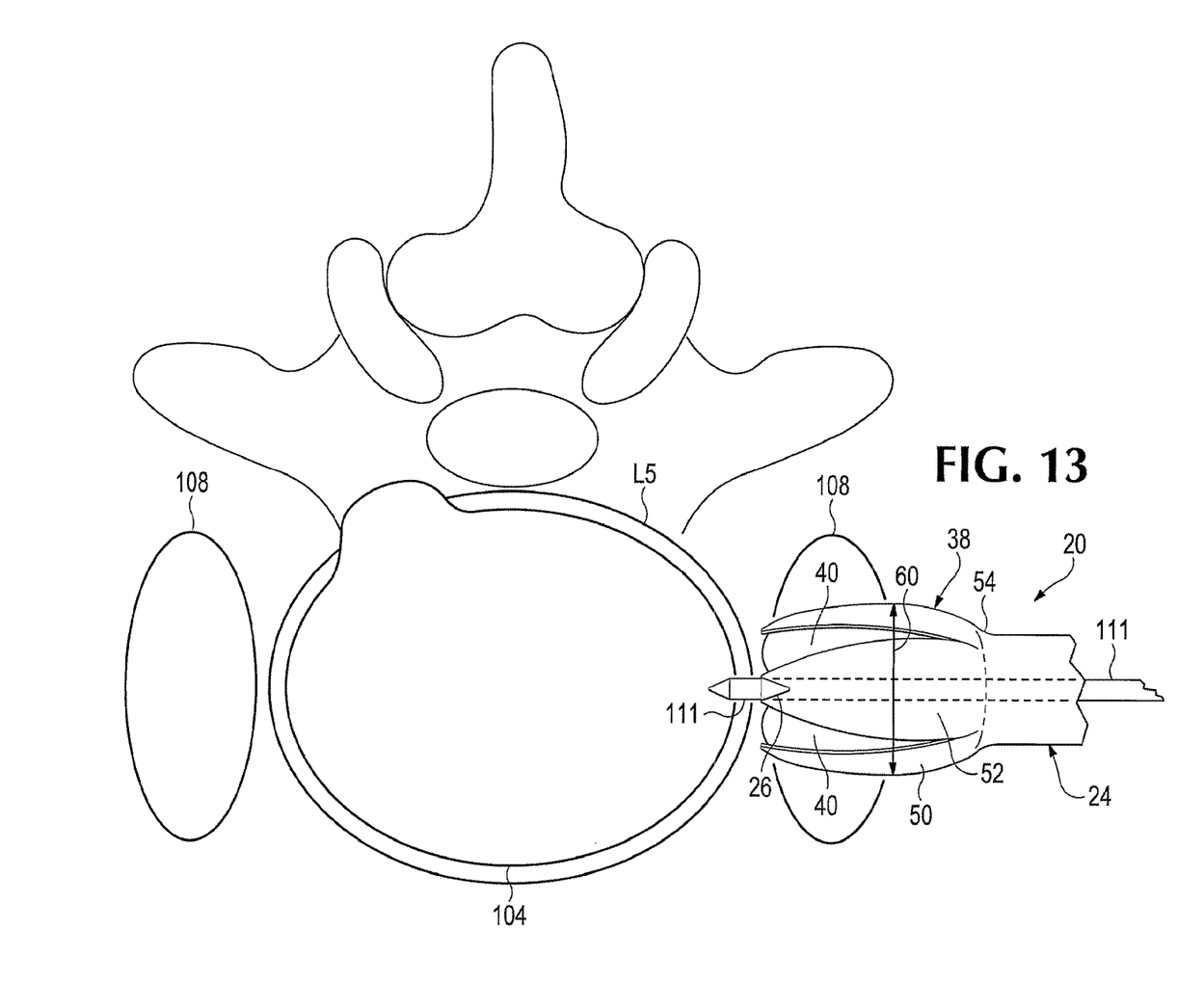
FIG. 13 is a simplified diagrammatic representation of a portion of a human spine, taken in the direction of line 13-13 in FIG. 12.

Referring next to FIGS. 12 and 13 of the drawings, the probe 20 or the probe 66 described above is intended to be useful particularly in connection with minimally invasive surgical techniques for spinal fusion. That is, the probe 20 or the probe 66 described above can be used in connection with removal of at least a portion of an intervertebral disc 104 from a patient's spinal column 106 and insertion of a spinal fusion support and spacer device (not shown), commonly called a cage, to maintain the desired separation between adjacent vertebrae and act as a foundation for osteogenesis, so that the adjacent vertebrae will fuse with each other and be located properly with respect to each other. The probes 20 and 66 including dilators 38 and 76 as described above are particularly useful in a lateral approach to the spinal column for fusion of the L4 and L5 vertebrae to each other.

As may be seen in FIG. 12, a large muscle, the psoas major muscle 108, is attached to the medial side of the femur and extends upward to attachment points 110, 112, 114 on the respective laterally-facing side of each of the vertebral bodies of all of the lumbar vertebrae.

In order to approach the spinal column in a minimally invasive manner, a small incision is made on the patient's side and extending into the body cavity, between the lowest rib and the top of the pelvis. The distal end of a probe 20 or 66 is inserted and the probe is pushed inward making its own entry path within the patient's peritoneum and guided visually by the surgeon toward a defective intervertebral disc that is to be removed, as shown schematically in FIG. 13. The correct location for entry and the appropriate path toward the disc 104 is initially determined, and thereafter may be monitored, radiographically as well as visually. When the probe 20 or 66 appears to be approaching the diseased intervertebral disc 104 as intended it is pushed through tissue adjacent to the lumbar vertebrae of the patient and further toward the intervertebral disc 104 to which surgical attention is intended. As the probe 20 or 66 approaches the spinal column, it must be pushed through the psoas major muscle 108, as may be seen best in FIG. 13.

Several significant nerves 116, 118 are located near the spinal column, originating from the spinal cord and extending between the spinal processes, passing between the portions of the psoas major muscle 108 and other major muscles in the vicinity of the spinal column. The probe 20 or 66 is intended to pass through the psoas muscle 108, leaving the nerves rearward of, or behind, the probe in the patient. Preferably the probe 20 or 66 is pushed through the psoas muscle so as to divide and push muscular fiber bundles apart, separating them, rather than severing muscle fibers, so as to minimize trauma and expedite eventual healing. In order not to cause any unnecessary trauma to the nerves, an electrical signal is provided to the electrode 26 or 74 by connecting a signal generator (not shown) to the associated terminal 32 or 74' for the conductor 30 or 75, as through the terminal ring 32 on the probe 20. The signal is delivered to the tissue surrounding the distal end portion 24 of the probe 20 or 66 through the electrode 26, and the response to the signal is noted by the surgeon to determine whether the probe 20 has to be repositioned in order to dilate tissue adjacent to the involved intervertebral disc without damaging a nerve. The location of the nerve can be determined by reference to the particular side of the probe 20 or 66 on which the electrode 26 or 74 is located, and correlating the response with the orientation of the electrode.

As the probe 20 or 66 is being inserted the psoas muscle 108 can be observed, and once the probe has been inserted through a portion of the psoas muscle 108 and its location relative to the nerves 116, 118 has been confirmed, the dilator 28 or 75 can be expanded.

Once the probe 20 has been placed properly into the psoas muscle 108, a quantity of fluid can be delivered into the interior space 44 within the bladder 40, using, for example, the syringe 48, to cause the sectors 50, 52, etc., of the distal end portion 24 to move outwardly away from the cannula 28, expanding a transverse dimension of a passageway created through the tissue and creating an enlarged space adjacent to the spinal column in which surgical tools may be utilized. Similarly, when the probe 66 has been inserted into the psoas major muscle 108 fluid can be delivered through the port 86 and thus into annular space 96 between the main body 82 and the cannula 70 to expand the bladder 76 to the configuration shown in FIGS. 9 and 10.

A guide wire 111, such as a K wire, can be fed through the cannula 28 or 70 and anchored in the intervertebral disc to immobilize the probe 20 or 66 while the dilator is being expanded and while a retractor is positioned to stabilize the tissues, including the psoas muscle. A retractor (not shown), such as a Nuvasive Maxxess retractor, may then be passed along the probe 20 or 66 and the dilator 38 or 75 of the probe 20 or 66 can be deflated, by use of the syringe 48 and the probe and inserted into the opening that has been created through psoas muscle to provide for visibility.

Thereafter, the guide wire 111, if used, can be withdrawn, leaving an open space created near the spinal column by expansion of the dilator portion 38 of the probe 20 and retained or further expanded by the retractor, and surgical tools and fiber optic lighting and viewing devices may be inserted. The spinal column 106, including the diseased or damaged defective disc 104 can then be seen. When desired, the probe can be used again on the same patient at the same or a different lumber or thoracic level of the spine.

Using the probe 20 or 66 for dilating the tissue in the locality where a path is required for visibility during a procedure, but not having to pass multiple tubular conventional dilators along a probe, offers a significant and valuable savings of time. It also reduces the amount of resulting damage to patient tissues not in the immediate vicinity of where a surgical procedure is to be performed.

Figure 14:
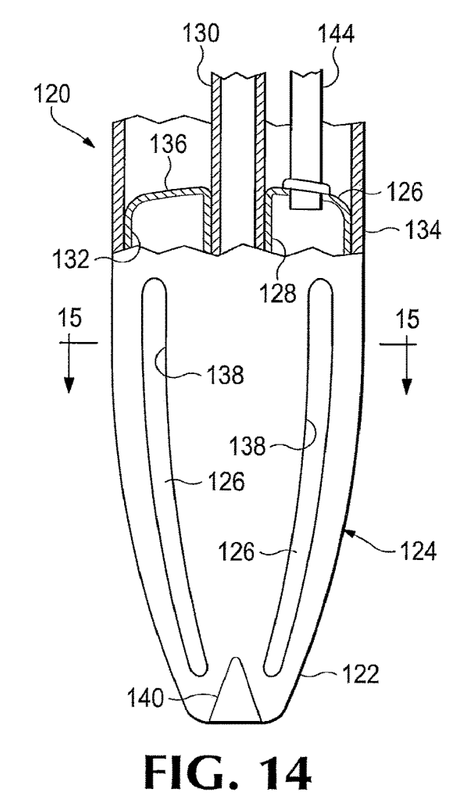
FIG. 14 is a side elevational view of a distal end portion of a probe that is another embodiment of an aspect of the invention.

A probe 120 including a dilator is shown in FIGS. 14-17. The proximal portions of the probe 120 may be essentially the same as those of the probe 20 and so only the distal end portion 122 is illustrated. A dilator portion 124 is included in the distal end portion 122, and includes an inflatable bladder 126 having a wall of a very elastic material. As shown in FIG. 14 the bladder 126 is elastically collapsed to its minimum size and resides within the distal end portion 122. A central tubular portion 128 of the bladder 126 surrounds and may be adhesively attached to the exterior of a cannula 130 extending longitudinally through the center of the interior of the probe 120, and an outer side wall portion 132 of the bladder 126 lies alongside an interior surface of the outer wall 134 of the body of the probe 120 and an upper part of the outer side wall portion may be adhesively attached to the outer wall 134. A top wall 136 of the bladder 126 may also encircle and be sealingly fastened to the exterior of the cannula 130.

Figure 15:
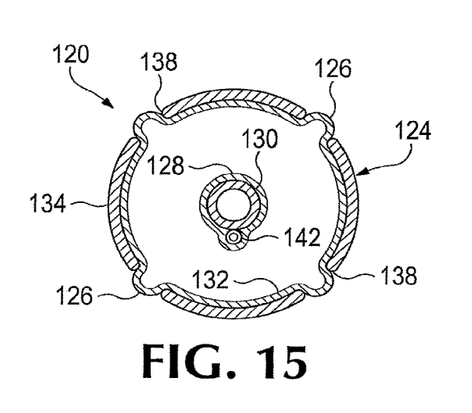
FIG. 15 is a sectional view taken on line 15-15 of FIG. 14.

Several slots 138 extend longitudinally along the distal end portion 122, preferably at regular angular intervals, exposing portions of the relaxed bladder 126 as shown in FIGS. 14 and 15. For example, there are four slots 138 shown in FIGS. 14, 15 and 17.

An electrode 140, similar to the electrode 26 is located on a tip end of the distal end 122, and is connected electrically through a conductor 142 extending longitudinally within the probe 120 alongside the exterior surface of the cannula 130, as may best be seen in FIG. 15, to be used in generally the same manner as in the probes 20 and 66.

Figure 16:
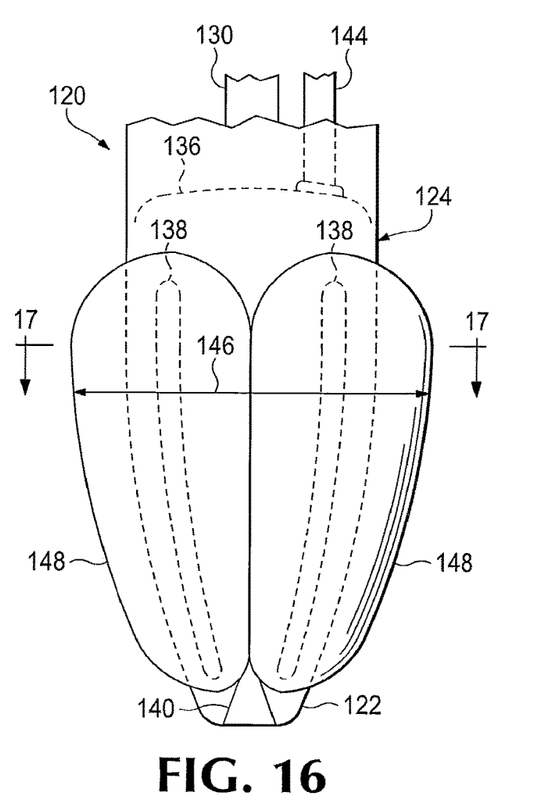
FIG. 16 is a side elevational view of the portion of a probe shown in FIG. 14, with a dilator portion of the probe in an expanded condition.
Figure 17:
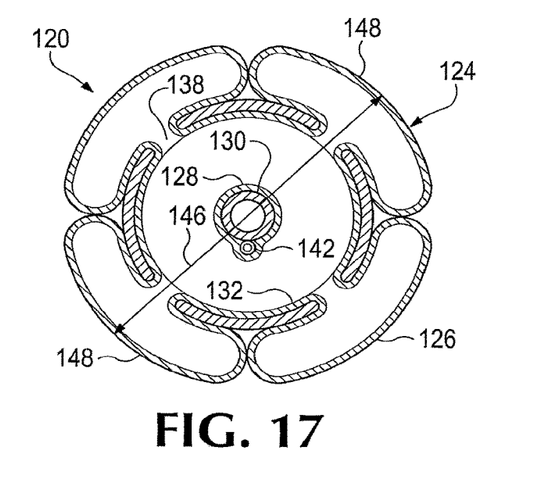
FIG. 17 is a sectional view taken on line 17-17 of FIG. 16.

The dilator 124 is utilized by inflating the bladder 126 by forcing a fluid into the interior of the bladder 126, through the fluid conduit 144 connected with the top wall 137, as shown in FIG. 14, thereby causing the bladder wall to expand elastically and protrude through each of the slots 138, as shown in FIGS. 16 and 17. As shown in FIG. 16, the expanded bladder, protruding through the slots 138, can produce an effective diameter 146 significantly greater than the diameter of the dilator portion 124 of the distal end 122 when the bladder is relaxed and retracted as shown in FIGS. 14 and 15. When inflated, the bladder 126, protruding through the slots 138, forms a separate inflated bubble-like element 148 associated with each of the slots 138, and with the proper choice of elastomeric material and the proper choice of spacing of and size of the slots 138 about the distal end 122 of the probe 120 the small inflated bubble-like elements 148 will widen toward, and eventually abut against, each other.

Flexibility of the small inflated elements 148 permits a retractor to be placed readily over the inflated dilator 124.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

I claim:

1. A minimally invasive method of accessing a human skeletal anatomy in order to perform a surgical procedure, comprising:
    providing an opening through a dermal layer;
    providing a probe having a main body, a distal end portion including a dilator, a cannula extending through the main body and the distal end portion, and a signal transmitter located at the distal end portion,
    passing the dilator through the opening and through a muscular tissue structure between the opening and the skeletal anatomy to which access is desired in order to perform the surgical procedure;
    determining when the distal end portion of the dilator has reached a proper intended location by applying a signal to tissue surrounding the distal end portion through the signal transmitter and evaluating a response thereto; and
    expanding the dilator radially and thereby increasing a transverse dimension of an opening through the tissue and thereby providing a pathway through the tissue as a passage to the skeletal anatomy.

2. The method of claim 1, wherein the signal transmitter includes an electrode and the step of determining includes applying an electrical signal through the electrode.

3. The method of claim 2, wherein the step of providing a probe includes providing a probe having an electrical conductor electrically connected with the electrode and extending to an electrical terminal associated with the main body of the probe.

4. The method of claim 1, wherein the step of expanding the dilator includes forcing a quantity of a fluid under pressure into an expandable member within the distal end portion, thereby expanding the distal end portion.

5. The method of claim 4, wherein the distal end portion includes a plurality of elongate segments each attached to the main body at a proximal end thereof and including the step of urging a distal end portion of each segment radially outward and apart from an outer end portion of an adjacent segment of the distal end portion.

6. The method of claim 1, wherein the distal end portion includes an elastomeric outer membrane, including the step of expanding the distal end portion radially from a first diameter similar to a diameter of the main body to a second diameter that is greater than the diameter of the main body.

7. The method of claim 2, wherein the electrode extends radially along a tip of the distal end portion.

8. The method of claim 1, wherein providing a probe includes providing a probe having an expansible member and wherein the expansible member is a hollow elastic body surrounding the cannula and configured to expand radially when a quantity of a fluid under pressure is introduced into the expansible member.

9. The method of claim 8, wherein the probe includes a conduit communicating with an interior of the expansible member and extending from the expansible member along the main body and having a proximal end available to be connected to a source of fluid under pressure.

10. The method of claim 1 wherein the probe further comprises an expansible member contained within the distal end portion when not inflated, and wherein the distal end portion defines a plurality of slots, portions of the expansible member protruding outward through the slots to act as the dilator when the expansible member is expanded.

* * * * *